United States Patent [19]

Visnjic

[11] Patent Number: 5,004,736
[45] Date of Patent: Apr. 2, 1991

[54] PROCEDURE FOR OBTAINING THE PREPARATION FOR THE TREATMENT OF THE DISEASE PSORIASIS: DRUG FOR THE TREATMENT OF PSORIASIS AND ITS APPLICATION

[76] Inventor: Pero Visnjic, Mose Pijade 3, 58300 Makarska, Yugoslavia

[21] Appl. No.: 370,121

[22] Filed: Jun. 23, 1989

Related U.S. Application Data

[63] Continuation of Ser. No. 875,221, Jun. 17, 1986, abandoned.

[30] Foreign Application Priority Data

Feb. 14, 1986 [YU] Yugoslavia ............................ 221/86

[51] Int. Cl.$^5$ ...................... A61K 31/62; A61K 31/56
[52] U.S. Cl. .................................... 514/161; 514/170; 514/863
[58] Field of Search ......................... 514/170, 863, 161

[56] References Cited

U.S. PATENT DOCUMENTS 3,934,013 1/1976 Poulsen ............................... 424/239
4,082,846 4/1978 Clark .................................... 424/266

FOREIGN PATENT DOCUMENTS 2116444 7/1972 France .
906000 9/1962 United Kingdom .
2084465 4/1982 United Kingdom .

OTHER PUBLICATIONS

Dictionnaire Vidal, "Disprosone Neomycine,"0 Topsyn Gras; 1974.
Unlisted Drugs "Diprogenta"; vol. 27, No. 1; 1975.
Chemical Abstracts; vol. 83 (1975) #103280j; Breche.
Unlisted Drugs, "Belosalic", vol. 31, No. 2, 1979.

Primary Examiner—Jerome D. Goldberg
Attorney, Agent, or Firm—Fleit, Jacobson, Cohn, Price, Holman & Stern

[57] ABSTRACT

The invention refers to the obtaining of the preparation for the treatment of the skin disease psoriasis. The object of the invention is a medicinal agent based on two corticosteroids, salicylates and antibiotics which clear the skin from psoriasis effectively, the most quickly and without endangering the integrity of healthy organs and skin regions and relapses approximate to zero point. The procedure according to the invention consists of the preparation of emulsion consisting of previously sterilized oil phase and water, to which are then added solutions of the active ingredients in such a way that all the phases are completed according to the order principle of ingredient stability to specified temperatures.

2 Claims, No Drawings

PROCEDURE FOR OBTAINING THE PREPARATION FOR THE TREATMENT OF THE DISEASE PSORIASIS: DRUG FOR THE TREATMENT OF PSORIASIS AND ITS APPLICATION

This application is a continuation of U.S. patent application Ser. No. 06/875,221, filed June 17, 1986 now abandoned.

BACKGROUND OF THE INVENTION

1. Field of the Invention

This invention relates to a composition for the treatment of psoriasis and methods for the manufacture and application of the composition.

2. Brief Description of the Prior Art

Skin diseases are as old as the human race and there has been an on-going search for curative agents. Plant extracts, as well as drugs of both organic and inorganic origin, have been used to treat these ailments.

At the present time, over 2000 preparations exist to treat psoriasis. Most of these are based on corticosteroids or combinations of antibiotics and salicylates. The prior art compositions containing corticosteroids, however, cause negative, secondary effects such as skin necrosis and steroidal dermatitis. Secondary effects on the adrenal gland, e.g., adrenal gland suppression, have also been observed.

SUMMARY OF THE INVENTION

Accordingly, an object of the present invention is to provide a composition for the treatment of psoriasis which eliminates undesirable, secondary effects on the endocrine system.

Another object of the present invention is to provide a method for manufacturing this composition and a method for its application.

In one embodiment, this invention provides a composition for the treatment of psoriasis which causes the disintegration of all kinds of crusts without causing skin necrosis. The composition, by neutralization of sugilation and subfusion processes, further induces vasoconstrictive effects on blood circulation, thereby enhancing recovery.

In another embodiment, the invention provides a method for preparing the composition.

Yet a further embodiment provides a method for the application of the claimed composition, in conjunction with adequate hygienic and dietetic measures to remove psoriatic crusts and prevent relapses.

DETAILED DESCRIPTION OF THE INVENTION

In order to further demonstrate the claimed invention, the following example is given as exemplary of the invention but without intending to limit the invention to this example.

The weighed components, usually used in the preparation of a vehicle for a medicinal ointment, are homogenized and melted at 150° C. While stirring, the ointment vehicle is cooled to 85°–90° C. This preparation phase lasts 20 minutes.

The ointment vehicle is filtered and added, with constant stirring, to demineralized water, which had been previously sterilized for 10 minutes. The emulsion resulting from the combination of the vehicle and water is sterilized for 30 minutes at 85°–90° C.

The emulsion is then cooled to 60° C. and the following active ingredients, previously dissolved in suitable solvents by aseptic procedures, are added, while stirring, in a ratio of 1:1.

9-fluoro-11, 17, 21-trihydroxy-16-methyl-pregna-1,4-diene-3, 20 dione-17, 21-diprorionate and also known as the corticosteroid betamethasone dipropionate and listed in Merck Index, 9th ed., Rahway, New Jersey, Merck & Co., 1976, p. 156, as 9-fluoro-11$\beta$, 17, 21-trihydroxy-16$\beta$ methylpregna-1, 4-diene-3, 20-dione 17, 21 dipropionate and 6, 9-difluoro-11, 16, 17, 21 tetrahydroxy-pregna-1,4-diene-3, 20-dion -21-acetate-16, 17-acetonide, also known as the corticosteroid fluocinonide and listed in Merck Index, 9th ed. Rahway, New Jersey, Merck & Co., 1976, p. 536, as 6$\alpha$, 9-difluoro-11$\beta$, 16$\alpha$, 17, 21-tetrahydroxy-pregna-1, 4-diene-3, 20-dione, cyclic 16, 17-acetal with acetone, 21-acetate.

The following ingredients are then added, while stirring:

gentamycin sulfate, at least 35,000 IU/100 g ointment,
vitamin A palmitate, 30,000 IU/100 g ointment,
2,4-dihydroxy-N-(3-hydroxypropyl)-3, 3-dimethyl butanamide, 0.5 g, also known as panthenol, and listed in the Merck Index, 9th ed., Rahway, New Jersey, Merck & Co., 1976, p. 386, as (R)-2, 4-Dihydroxy-N-(3-hydroxy-propyl)-3, 3-dimethyl-butanamide.

After further stirring and homogenization, salicylic acid, in an amount equivalent to 7% of 100 g of ointment is added. The emulsion is then again subjected to homogenization and cooling.

The composition prepared according to the above method proved to be very effective in topically treating psoriasis and preventing relapses when utilized in conjunction with certain dietary regimens.

I claim:

1. A process for preparing a medicinal ointment for the treatment of psoriasis, consisting of the steps of:

preparing a vehicle for a medicinal ointment by homogenizing the ingredients, melting at 150° C., and cooling to 85°–90° C., with stirring for 20 minutes, emulsifying the vehicle with demineralized sterile water, sterilizing the resultant emulsion 30 minutes at 85°–90° C., cooling the emulsion to 60° C., adding 9-fluoro-11$\beta$,17,21-trihydroxy-16$\beta$-methyl-pregna-1,4-diene-3,20-dion-17,21-dipropionate and 6,9-difluoro-11,16,17,21-tetrahydroxy-pregna-1,4-diene-3,20-dion-21-acetate-16,17-acetonide dissolved in suitable sterile solvents to the emulsion, while stirring, said 9-fluoro-11$\beta$,17,21-trihydroxy-16$\beta$-methyl-pregna-1,4-diene-3,20 -dion-17,21-dipropionate and, 6,9-difluoro-11,16,17,21-tetrahydroxy-pregna-1,4-diene-3,20-dion-21-acetate-16,17-acetonide being added in a ratio of 1:1; and then adding the following ingredients, while stirring: gentamycin sulfate, vitamin A palmitate wherein the gentamycin sulfate is added in an amount equivalent to at least 35000 IU/100 g of the ointment, and wherein vitamin A palmitate is added in an amount equivalent to 30000 IU/100 g of the ointment, and 2,4-dihydroxy-N-(3-hydroxypropyl)-3,3-dimethyl-butanamide, 0.5 g per 100 g of ointment; and then adding salicylic acid at 7% by weight of the ointment; and homogenizing and cooling the resulting medicinal ointment.

2. A medicinal ointment for the treatment of psoriasis which is obtained by the process according to claim 1.

* * * * *